United States Patent
Kaizik et al.

(10) Patent No.: US 8,563,782 B2
(45) Date of Patent: Oct. 22, 2013

(54) PRODUCING α,β-UNSATURATED ALDEHYDES BY MEANS OF A REACTION MIXING PUMP

(75) Inventors: Alfred Kaizik, Marl (DE); Hans-Gerd Lueken, Marl (DE); Dirk Fridag, Haltern am See (DE); Wilfried Bueschken, Haltern am See (DE); Dirk Mackowiak, Borken (DE); Frank Brocksien, Duelmen (DE)

(73) Assignee: Evonik Oxeno GmbH, Marl (DE)

( * ) Notice: Subject to any disclaimer, the term of this patent is extended or adjusted under 35 U.S.C. 154(b) by 49 days.

(21) Appl. No.: 13/498,690

(22) PCT Filed: Aug. 3, 2010

(86) PCT No.: PCT/EP2010/061238
§ 371 (c)(1),
(2), (4) Date: Mar. 28, 2012

(87) PCT Pub. No.: WO2011/038957
PCT Pub. Date: Apr. 7, 2011

(65) Prior Publication Data
US 2012/0190895 A1 Jul. 26, 2012

(30) Foreign Application Priority Data
Sep. 30, 2009 (DE) .......................... 10 2009 045 139

(51) Int. Cl.
*C07C 45/72* (2006.01)
(52) U.S. Cl.
USPC ........................................................ 568/461
(58) Field of Classification Search
USPC ........................................................ 568/461
See application file for complete search history.

(56) References Cited

U.S. PATENT DOCUMENTS

| | | |
|---|---|---|
| 6,680,414 B2 | 1/2004 | Knoop et al. |
| 7,138,552 B2 | 11/2006 | Kaizik et al. |
| 7,524,997 B2 | 4/2009 | Kaizik et al. |
| 8,138,379 B2 | 3/2012 | Lueken et al. |
| 2004/0138510 A1 | 7/2004 | Kramarz et al. |
| 2006/0161017 A1 | 7/2006 | Grass et al. |
| 2011/0060169 A1 | 3/2011 | Kaizik et al. |
| 2011/0130595 A1 | 6/2011 | Lueken et al. |
| 2012/0035382 A1 | 2/2012 | Priske et al. |

FOREIGN PATENT DOCUMENTS

| | | |
|---|---|---|
| DE | 42 20 239 | 12/1993 |
| EP | 0 070 529 | 1/1983 |
| WO | 2004 065342 | 8/2004 |

OTHER PUBLICATIONS

U.S. Appl. No. 13/703,925, filed Dec. 13, 2012, Franke, et al.
Fink, et al., "Pumpen, Die Mitmischen", Chemie Technik, pp. 52-54, XP-002599179, Jul. 2007.
International Search Report issued on Oct. 1, 2010 in PCT/EP10/061238 filed on Aug. 3, 2010.
U.S. Appl. No. 13/386,523, filed Jan. 23, 2012, Grass, et al.
U.S. Appl. No. 13/256,116, filed Sep. 27, 2011, Kaizik, et al.
U.S. Appl. No. 13/502,226, filed Apr. 16, 2012, Kaizik, et al.
U.S. Appl. No. 13/822,650, filed Mar. 13, 2013, Franke, et al.
U.S. Appl. No. 13/988,431, filed May 20, 2013, Nordhoff, et al.
U.S. Appl. No. 13/883,808, filed May 7, 2013, Franke, et al.

*Primary Examiner* — Sikarl Witherspoon
(74) *Attorney, Agent, or Firm* — Oblon, Spivak, McClelland, Maier & Neustadt, L.L.P.

(57) ABSTRACT

The invention relates to a method for producing α,β-unsaturated aldehydes, wherein a catalytic aldol condensation of charged aldehydes is carried out in the presence of an aqueous base within a continuous-flow reactor. The aim of the invention is to provide a method for aldolizing aldehydes that can be carried out in a particularly economical manner. The aim is achieved by using a reaction mixing pump as the reactor.

19 Claims, 2 Drawing Sheets

PRODUCING α,β-UNSATURATED ALDEHYDES BY MEANS OF A REACTION MIXING PUMP

Figure 1:
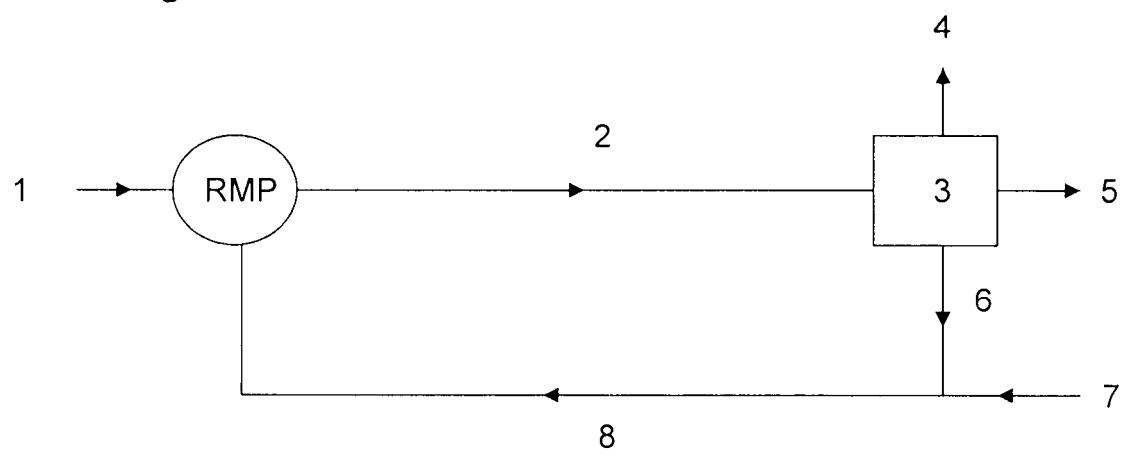

The invention relates to a process for preparing α,β-unsaturated aldehydes, in which a catalytic aldol condensation of starting aldehydes in the presence of an aqueous base is carried out within a reactor through which continuous flow occurs.

Such a process is known from WO 2004/065342 A1

Unsaturated aldehydes are, because of their reactivity, starting materials for preparing many organic compounds. Selective hydrogenation of them gives the corresponding saturated aldehydes which are likewise the basis of many syntheses. Oxidation of the aldehydes leads to carboxylic acids which are utilized industrially. Hydrogenation of the aldehydes leads to saturated alcohols which are used for producing plasticizers and detergents.

The aldol reaction of n-butyraldehyde with simultaneous elimination of water to form 2-ethylhexenal is carried out worldwide on a large scale since the hydrogenation product, viz. 2-ethylhexanol, is used in large quantities as plasticizer alcohol. As catalyst, use is usually made of a base dissolved in water. The use of aqueous sodium hydroxide having an NaOH content in the percentage range is typical. The reaction is frequently carried out in a temperature range of 80-150° C., a pressure of less than 5 bar and a phase ratio of organic phase to aqueous catalyst phase of from 1 to 20 (Hydrocarbon Processing, October 1980, Section 2, pages 93-102). This reaction can, for example, be carried out in a stirred vessel (DE 19 06 850, DE 927 626), in a packed column which is operated in countercurrent (G. Dümbgen, D. Neubauer, Chemie-Ing.-Techn., 41, 974 (1969)), or in a flow tube (GB 761 203). All these processes give 2-ethylhexenal in a selectivity of up to 98% at conversions of 98.5%. A disadvantage is that at relatively high temperatures, part of the n-butyraldehyde used is irreversibly lost as a result of the Cannizzaro reaction. The butyric acid formed in the Cannizzaro reaction neutralizes the basic catalyst. Part of the catalyst solution containing a high burden of organic material therefore has to be continually discharged and replaced by fresh catalyst.

In a manner analogous to n-butyraldehyde, n-pentanal (n-valeraldehyde) can be converted into the unsaturated $C_{10}$-aldehyde 2-propyl-heptenal. The aldol condensation of the $C_5$-aldehyde can be carried out in stirred reactors which are equipped with internal heat exchangers to remove the heat. This method of carrying out the reaction is described, for example, in WO 93/20034 A1 and is, owing to the moving parts, mechanically susceptible and complicated to construct and maintain because of the built-in heat exchanger in the reactor.

A characteristic of the aldol condensation of aldehydes is the participation in the reaction of two liquid phases (organic aldehyde phase, aqueous catalyst phase) which are virtually immiscible. To achieve high conversions and selectivities, it is therefore necessary for the two mutually immiscible liquid phases to be brought into intimate contact with one another during the reaction in order to overcome the mass transfer limitation between the phases. A very large mass transfer area between the two phases therefore has to be generated by means of suitable process engineering measures.

According to the prior art presented in WO 93/20034 A1, the mass transfer between the organic aldehyde-containing phase and the aqueous catalyst phase is ensured when using stirred vessels by intensive stirring and when using tube reactors by turbulent flow.

However, stirring in a stirred vessel requires input of mechanical energy to drive the stirrers. To reduce the production costs, it is desirable to introduce the mechanical stirring work required to maintain the reaction very effectively in order to reduce the total energy consumption.

It is known from WO 2004/065342 A1 that the aldolization can be carried out in a reactor which is made up of a tube and a segment having fixed turbulence-generating elements. A centrifugal pump allows the reaction mixture to be circulated through the tube, as a result of which turbulence is generated at the turbulence-generating elements. The turbulent flow of the reaction liquid leads to turbulent mixing of its phases, which makes mass transfer between them possible. The apparatus described here is possibly a loop reactor. Comparative examples to indicate whether the turbulence-generating effectiveness of such an aldolization reactor is better than that of a reactor having rotating stirrers are not presented.

In any case, the construction of an aldolization reactor with fixed turbulence-generating elements arranged outside the centrifugal pump, as described in WO 2004/065342 A1, has the disadvantage of a large holdup. The holdup of an apparatus through which flow occurs in operation is the volume of fluid which remains in the apparatus in the rest state of the plant with pumps switched off. The holdup of the aldolization reactor disclosed in WO 2004/065342 A1 is made up of the volume of the lines, the volume of the turbulence-generating sector and of the pump housing.

Thanks to their small holdup, reaction mixing pumps are attractive as reactor for the continuous reaction of reactive and toxic reactants.

A reaction mixing pump in the sense used here comprises:
a) a fixed pump housing,
b) an impeller which is mounted so as to be able to rotate in the pump housing and has a plurality of radially extending mixing chambers which are open in the direction of the circumference of the impeller,
c) a mixing channel which encloses the mixing chambers and extends within the pump housing along the circumference of the impeller,
d) at least one inlet for reaction starting materials and an outlet for reaction products, with inlet and outlet being connected so as to allow fluid flow by the mixing channel,
e) a motor, by means of which the impeller can be rotated.

The following reports on carrying out reactions by means of reaction mixing pumps have hitherto appeared:
Reaction of phosgene in Fink, Dieter and Wölfert, Andreas: Pumpen, die mitmischen. Chemie Technik, July 2007, pages 52-54.
Polycarbonate production in DE102008008841A1.
Conversion of pseudoionones into the corresponding ionones in WO 97/43254. However, this is a cyclization under acidic conditions, not an aldol condensation under alkaline conditions.

However, carrying out aldolizations by means of reaction mixing pumps has not become known hitherto.

In the light of this prior art, it is an object of the invention to provide a process for the aldolization of aldehydes which can be operated particularly economically.

The object is achieved by using a reaction mixing pump as reactor.

The invention therefore provides a process for preparing α,β-unsaturated aldehydes, in which a catalytic aldol condensation of starting aldehydes in the presence of an aqueous base is carried out within a reactor through which continuous flow occurs, wherein the reactor is a reaction mixing pump.

The pump here serves not only as means of transporting alkali, aldehyde and product but at the same time also as reactor.

Carrying out an aldol condensation by means of a reaction mixing pump exceeds expectations as to the economics of the process to a surprising degree. This may be attributed to the fact that the reaction mixing pump simultaneously exercises a positive influence on three factors related to the economics of the process: firstly, mention may be made of the comparatively small holdup of a reaction mixing pump, which reduces the dead proportion of the invested capital. Furthermore, the specific mechanical energy consumption of the reaction mixing pump is low since it achieves effective generation of turbulence. Finally, there is surprisingly an improved selectivity, i.e. a better yield of the α,β-unsaturated aldehydes to be produced with low formation of undesirable by-products. The latter effect in particular was not foreseeable.

Overall, the advantages of the process of the invention are the high yield of α,β-unsaturated aldehydes in a single pass and the small space requirement of the sub-plant for preparing the mixture of crude α,β-unsaturated aldehydes (mixture before distillation) and the lower capital investment compared to a plant having a conventional reactor.

Advantageous embodiments of the invention are set forth in the dependent claims and can be derived from the description which now follows and the examples.

Starting Materials

The process of the invention is suitable for the reaction of aldehydes or aldehyde mixtures which can undergo condensation reactions. If only one aldehyde is used, this has to have two a-hydrogen atoms on the same carbon atom next to the CO group. If two or more different aldehydes are used, at least one of the aldehydes has to have two α-hydrogen atoms on the same carbon atom.

Aldehydes having two α-hydrogen atoms according to the above definition are, for example: acetaldehyde, propanal, n-butyraldehyde, n-valeraldehyde, 3-methylbutyraldehyde, n-hexanal, 3-methylpentanal, 4-methylpentanal, n-heptanal, n-octanal, n-nonanal, n-decanal. These are also suitable for a homocondensation.

Examples of aldehydes having one α-hydrogen atom according to the above definition are: isobutyraldehyde, 2-methylbutyraldehyde, 2-methylpentanal, 2-ethylhexanal, cyclohexylaldehyde. Examples of aldehydes having no a-hydrogen atom are: benzaldehyde, 2,2-dimethylpropanal and formaldehyde. The aldehydes of the two last-named groups can undergo an aldol condensation only with an aldehyde having two α-hydrogen atoms.

Preferred starting aldehydes for the process of the invention are: n-butyraldehyde, n-valeraldehyde, a mixture of n-butyraldehyde and isobutyraldehyde, mixtures of n-valeraldehyde with 2-methylbutyraldehyde or 3-methylbutyraldehyde or the corresponding three-component mixtures. In particular, use is made of $C_5$-aldehyde mixtures containing more than 90% by mass of n-pentanal, very particularly preferably more than 95% by mass of n-pentanal. It is likewise possible to use a mixture of $C_4$- and $C_5$-aldehydes. These aldehydes can, for example, be prepared by hydroformylation of olefins.

When more than one aldehyde or an aldehyde mixture is used, the individual components can be fed separately, preferably in the pump, into the stream of the catalyst solution. It is likewise possible to mix all starting materials before introduction and feed them in together. Furthermore, the aldehydes can be used as a solution. As solvents, it is possible to use inert liquids which have little solubility in the catalyst solution, e.g. hydrocarbons (pentane, cyclohexane, toluene).

As catalyst in the process of the invention, it is possible to use water-soluble, basic compounds such as hydroxides, hydrogencarbonates, carbonates, carboxylates or mixtures thereof in the form of their alkali metal or alkaline earth metal compounds. Preference is given to using alkali metal hydroxides such as sodium hydroxide.

The concentration of the catalyst in the continuous phase is in the range from 0.1 to 15% by mass, in particular from 0.3 to 5% by mass.

If pentanals are converted into decenals by the process of the invention, sodium hydroxide is preferably used as catalyst. A small part of the sodium hydroxide is discharged together with the water of the reaction which is discharged. To compensate for the losses of sodium hydroxide, fresh sodium hydroxide is introduced. Here, the fresh sodium hydroxide together with the recycle alkali forms the process alkali which is fed into the reaction mixing pump. The recycle alkali contains sodium hydroxide together with sodium salts of carboxylic acids, mainly pentanoic acids. The carboxylic acid salts have essentially been formed by the Cannizzaro reaction.

In the process of the invention, the sodium content of the process alkali at the reactor inlet in the preparation of decenals is from 0.60 to 1.75% by mass, in particular from 1.1 to 1.20% by mass. To adjust the sodium concentration of the process alkali, fresh sodium hydroxide solution having a concentration of greater than 2.5% by mass is introduced into the recycle alkali. To introduce a little water into the reaction system, preference is given to using sodium hydroxide solution having a relatively high concentration. In the process of the invention, sodium hydroxide solution having a concentration in the range from 5 to 30% by mass, for example 10% by mass, is preferably used.

Reaction Mixing Pump

A reaction mixing pump is used for transporting starting material(s), products and catalyst solution and also for carrying out the reaction in the process of the invention for preparing unsaturated aldehydes by aldol condensation. The reaction mixing pump is in the broadest sense a peripheral wheel pump having a plurality of inlets (transport channels) for starting materials and catalyst solution in the circumferential wall of the mixing chamber of the pump and also an outlet for the reaction mixture. These apparatuses have the properties of a pump, of an effective mixer and of a reactor. Some of these apparatuses are provided with cooling and/or heating devices or can be thermostatted in another way, so that reactions can be carried out therein at desired temperatures.

The structure and functional principle of reaction mixing pumps are described in the technical literature (D. Fink, A. Wölfert, Chemie Technik, July 2007, pages 52-54).

The typical reaction mixing pump (reaction mixer) consists essentially of the drive, the pump housing and the mixing rotor (impeller) present therein. The impeller is driven by the motor, preferably via a magnetic coupling. The chambers (transport cells) arranged radially on both sides of the impeller, the respective inlet (transport channel) and a baffle lead to the typical transport and mixing behavior of reaction mixing pumps. The transport cells on the mixing rotor together with the ring-shaped channels at the end faces of the mixing chamber form the pressure cells typical of a peripheral wheel. The pronounced turbulence in the transport and reaction space leads by mutual interaction to continual exchange of the faster moving liquid content of the pressure cells with the more slowly flowing liquid stream in the region of the transport channels and thus to intensive mixing of the liquids. This mixing produces a homogeneous and stable mixture which is continuously discharged through the outlet. This pronounced momentum exchange and mixing effect of the reaction pump is employed in the present invention for carrying out the aldol condensation of aldehydes.

As is shown for the example of the process of the invention, the use of reaction pumps is especially preferred when highly chemically reactive components are to be mixed and homogeneously distributed for the reaction. Depending on the reaction conditions and process engineering boundary conditions, the reaction mixers can be equipped with special devices. Thus, for example, the pump heads can, depending on the viscosity and reactivity of the starting materials or depending on the reaction time, be equipped with additional residence chambers and premixing chambers or with additional inlets for recirculation of intermediates into the transport space.

Reaction Conditions

According to the invention, the aldol condensation is carried out in the temperature range from 50 to 160° C. If pentanals are converted into decenals, the reaction temperature is in the range from 100 to 150° C., in particular in the range from 110 to 140° C., very particularly preferably in the range from 120 to 140° C.

The reaction pressure in the reaction mixing pump is at least so high that both the process alkali and the organic materials (starting material, product and optionally solvent) are in each case present as liquid phase. In the conversion of pentanals into decenals, the pressure in the reaction mixing pump is from 0.1 to 2 MPa, in particular from 0.3 to 1 MPa, very particularly preferably from 0.3 to 0.5 MPa.

The ratio [kg/kg] of process alkali to starting material at the pump inlet is in the range from 5 to 500, in particular in the range from 20 to 400. In the conversion of pentanals into decenals, this ratio is from 10 to 300, in particular 40 to 240.

In the process of the invention, the average residence time of the liquid (organic and aqueous phases) in the reaction mixing pump is, assuming that both phases flow at the same speed, in the range from 0.05 to 3 seconds, in particular in the range from 0.1 to 2 seconds. In the conversion of pentanals into decenals, the average residence time is preferably from 0.1 to 1.5 seconds, in particular from 0.1 to 1 second, very particularly preferably from 0.2 to 0.5 second.

Work-Up

The output from the pump is cooled and the organic phase is separated from the alkali phase. The phase separation is carried out in the temperature range from 20 to 130° C.

When a decenal mixture, formed from pentanals, is separated off, the phase separation is carried out in the temperature range from 60 to 130° C., in particular in the range from 70 to 120° C., very particularly preferably in the range from 90 to 110° C.

To separate the heavy, aqueous phase from the light, organic phase, it is possible to use separators which make phase separation possible with sole utilization of gravity. These gravity separators can also be provided with coalescence-promoting internals to improve the separation performance. The use of internals accelerates the coalescence and sedimentation process. As coalescence aids, it is possible to use, for example, plates, packing elements, mesh packings or fiber bed precipitators. Gravity separators can be configured as essentially horizontal vessels or as upright vessels.

As an alternative to gravity separators, it is possible to use separators operating according to the centrifugal principle for liquid-liquid separation. The heavy phase is separated off by means of centrifugal forces in a rotating drum.

In order to separate off the heavy, aqueous phase, preference is given to using gravity separators, preferably gravity separators configured as essentially horizontal vessels with internals, in the process of the invention.

Part of the alkali phase which has been separated off is discharged to remove water of reaction, and the other part is recirculated to the reactor. Part of the carboxylic acids formed as by-products (as sodium salts) and sodium hydroxide are also separated off with the discharge stream. This stream can be passed to a water treatment plant. However, it is also possible to work up this stream and recirculate part of it to the process, as described, for example, in DE 198 49 922 and DE 198 49 924.

If the organic phase contains not only the aldol condensation products and small amounts of unreacted starting material but also other by-products such as carboxylic acid salts, sodium hydroxide and dissolved water, traces of base and part of the carboxylic acid salts can be removed by means of a water scrub. The water extract obtained here can be used for making up the fresh alkali (not shown in FIGS. 1 and 2).

The organic phase can be worked up by distillation. The starting materials separated off here can be partly recirculated to the reaction mixing pump.

The $\alpha,\beta$-unsaturated aldehydes produced can be used for preparing carboxylic acids (by hydrogenation of the olefinic double bond and oxidation of the aldehyde group) or for preparing primary alcohols (by total hydrogenation).

In the preparation of primary alcohols, the crude mixture can also optionally be hydrogenated and the fractional distillation can be carried out after the hydrogenation.

A further option in the present invention is to subject the reaction mixture to a flash distillation after leaving the reactor and before the phase separation. Here, the hot reaction mixture is depressurized into a vessel.

A mixture of water and mainly starting material is obtained as distillate and this can be completely or partly recirculated to the reactor. (Separation of the distillate and recirculation of part of the organic distillate is not shown in FIG. 2). Such a process is described, for example, in DE 199 56 410.

Process Variants

The present invention is described in more detail below with the aid of FIGS. 1 and 2.

A block diagram of an embodiment in which the process of the invention can be carried out is shown in FIG. 1. The starting aldehydes as starting material (1) and the aqueous base as catalytically active process alkali (8), comprising recycle alkali (6) and fresh alkali (7), is drawn in by the reaction mixing pump (RMP). The aldol condensation takes place in the reaction mixing pump (RMP). The output (2) from the pump is separated in the separation vessel (3) into an organic phase (4) containing the target product and an alkali phase of which part (5) is discharged and the other part (6) is recirculated to the reaction mixing pump (RMP).

Figure 2:
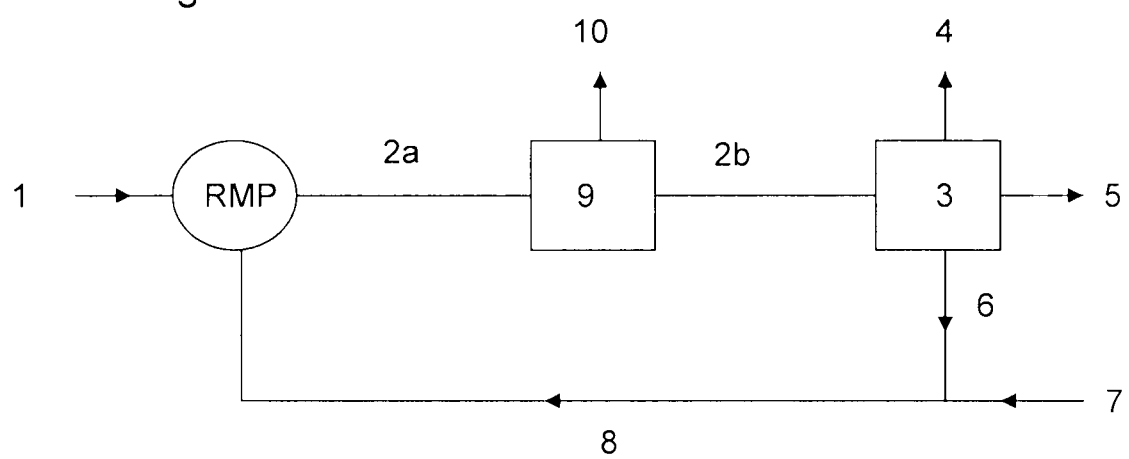

FIG. 2 shows a further embodiment of the process of the invention. The process variant in FIG. 2 differs from the variant in FIG. 1 in that the output (2) from the pump is subjected to a flash distillation in the apparatus (9), where part of the low boilers (10), mainly unreacted starting material, is separated off, before the phase separation in the vessel (3).

EXAMPLES

The following examples illustrate the invention without restricting its scope which is defined by the description and the claims.

Experimental Apparatus

The aldol condensation of $C_5$-aldehydes according to the process of the invention was carried out in an experimental plant, corresponding schematically to the process variant shown in FIG. 1.

The continuous catalyst phase (recycle alkali) 6 and 7 (fresh sodium hydroxide solution) is fed via an inlet into the reaction mixing pump model HR060 from Fink and circulated. The $C_5$-aldehyde (n-pentanal) was mixed in from line 1 via a second inlet on the reaction pump. The liquid stream obtained downstream of the reaction pump (product and catalyst phases) was conveyed via line 2 into a phase separation vessel 3. Here, the aqueous catalyst phase (lower phase) was separated off and returned via line 6 to the circuit. The organic phase (upper phase), which contains the reaction product, can be taken off via line 4. The water of reaction formed can be discharged continuously via line 5. To compensate for the losses of sodium hydroxide due to discharge of the water of reaction, fresh 10% strength sodium hydroxide solution is continuously introduced via line 7. The heat of reaction was removed via the heat exchangers located outside the reactor (not shown in FIG. 1). To carry out a comparative aldol condensation of pentanals which is not according to the invention, a stirred reactor was used as reactor instead of a reaction mixing pump, as described in example 1.

The tables accompanying examples 1 and 2 show the reaction conditions of the $C_5$-aldehyde condensation in the upper part of the tables. In the lower part of the table for each example, the product composition is likewise listed in % by mass from the GC analysis. In the interests of clarity, no distinction is made between the isomers of the individual $C_{10}$-aldehydes and $C_{10}$-hydroxyalkanals (aldols). These values are summarized as "2-propylheptenal" and "$C_{10}$-aldol". The by-products of the aldolization, e.g. trimers and tetramers which have come from the aldol reaction (addition and condensation) of three or four $C_5$-aldehydes, are likewise summarized as "high boilers/miscellaneous".

Example 1

Comparative Example

Preparation of 2-Propylheptenal from N-Pentanal in a Stirred Reactor 2-propylheptenal was prepared by condensation of n-pentanal in a stirred reactor in the form of an extraction column (volume 2.1 liters) having 10 mixing chambers, which were equipped with a 4-blade stirrer mounted on a stirrer shaft. The continuous catalyst phase (2% strength sodium hydroxide solution) was circulated by means of a circulation pump. The starting material n-valeraldehyde was taken from a 100 l drum (starting material reservoir) and pumped continuously through a thin capillary into the NaOH circuit upstream of the reactor inlet. The mixture of product phase and aqueous catalyst phase was fed to a phase separation vessel downstream of the reactor. In the phase separation vessel, the organic product phase was separated from the catalyst phase at 80° C. After the product phase had been separated off, the aqueous phase was introduced into the NaOH circuit.

The catalyst circulation (2.0% strength aqueous NaOH) was 80 l/h in all experiments. The starting material n-pentanal was fed at a throughput of 8 l/h, corresponding to a phase ratio (PR) of organic phase to aqueous phase of 1:10, into the NaOH circuit. The starting material contained 99.12% by mass of n-pentanal, and also 0.88% by mass of secondary components including 0.70% by mass of high boilers/miscellaneous.

Table 1 below shows the results of the aldolization of n-pentanal at three temperatures 110° C., 120° C. and 130° C., and a pressure of 4 bar at a stirrer speed of 2000 rpm (unit: revolutions per minute/rpm). In continuous operation after a time of 3 hours in the steady state, the following results were obtained:

TABLE 1

| Aldolization of n-pentanal in a stirred vessel | | | |
|---|---|---|---|
| Reaction conditions | | | |
| n-Pentanal (l/h) | 8 | 8 | 8 |
| Temperature (° C.) | 110 | 120 | 130 |
| PR (l of starting material/l of cat. phase) | 1:10 | 1:10 | 1:10 |
| Product composition | | | |
| n-Pentanal (% by mass) | 6.33 | 5.34 | 4.43 |
| n-Pentanol (% by mass) | 0.12 | 0.10 | 0.11 |
| 2-Propylheptenal (% by mass) | 90.86 | 92.04 | 93.27 |
| $C_{10}$-aldols (% by mass) | 0.93 | 0.58 | 0.00 |
| High boilers/miscellaneous (% by mass) | 1.76 | 1.93 | 2.20 |
| n-Pentanal conversion (%) | 93.6 | 94.6 | 95.5 |
| Selectivity (%) | 97.9 | 98.1 | 98.5 |

As can be seen from the table, the n-pentanal conversion increases with increasing reaction temperature. To achieve high n-pentanal conversions of greater than 95%, reaction temperatures above 120° C. are required under the selected reaction conditions.

Example 2

According to the Invention

Preparation of 2-Propylheptenal from N-Pentanal in a Reaction Mixing Pump

In the following example, the preparation of 2-propylheptenal by condensation of n-pentanal in a reaction mixing pump is described. A reaction pump model HR060 from Fink having a heated housing and a pump stroke of about 15 ml was used as reaction mixer.

The continuous catalyst phase (2% strength sodium hydroxide solution) was introduced into the reaction mixing pump via an inlet. The starting material n-valeraldehyde was taken from a 100 l drum (starting material reservoir) and pumped continuously via a second inlet into the mixing chamber of the reaction pump. The mixture of the product phase and aqueous catalyst phase was discharged from the reaction pump via an outlet and conveyed via a stainless steel line (2 m length, 12 mm internal diameter) to a phase separation vessel. In the phase separation vessel, the organic product phase was separated from the catalyst phase at 80° C. After the product phase had been separated off, the aqueous phase was introduced into the NaOH circuit.

The catalyst circulation (2.0% strength aqueous NaOH) of 160 was kept constant at all experimental settings. The starting material n-pentanal was fed at a throughput of 2 l/h into the reaction mixer, corresponding to a phase ratio (PR) of organic phase to aqueous phase of 1:80. The starting material contained 98.82% by mass of n-pentanal, and also 1.18% by mass of secondary components including 0.07% by mass of n-Pentanol, 0.53% by mass of 2-propylheptenal and 0.58% by mass of high boilers/miscellaneous.

Table 2 below shows the results of the aldolization of n-pentanal at three reaction temperatures of 110° C., 120° C. and 130° C., and a pressure of 5 bar.

In continuous operation after a time of 3 hours in the steady state, the following results were obtained:

TABLE 2

Aldolization of n-pentanal in a reaction mixing pump

| Reaction conditions | | | |
|---|---|---|---|
| n-Pentanal (l/h) | 2 | 2 | 2 |
| Temperature (° C.) | 110 | 120 | 130 |
| PR (l of starting material/l of cat. phase) | 1:80 | 1:80 | 1:80 |
| Product composition | | | |
| n-Pentanal (% by mass) | 5.91 | 5.24 | 4.36 |
| n-Pentanol (% by mass) | 0.10 | 0.10 | 0.11 |
| 2-Propylheptenal (% by mass) | 89.98 | 91.69 | 93.43 |
| $C_{10}$-aldols (% by mass) | 2.95 | 1.88 | 0.96 |
| High boilers/miscellaneous (% by mass) | 1.05 | 1.09 | 1.15 |
| n-Pentanal conversion (%) | 94.0 | 94.7 | 95.6 |
| Selectivity (%) | 96.3 | 97.4 | 98.3 |

As can be seen from the table, high n-pentanal conversions of >94% and 2-propylheptenal selectivities of >97% are achieved when using a reaction pump for the aldolization of n-pentanal under the selected reaction conditions at temperatures above 120° C. despite a lower reaction volume.

Example 3

According to the Invention

Preparation of 2-Propylheptenal from N-Pentanal in a Reaction Mixing Pump

The following example presents the preparation of 2-propylheptenal at a pentanal throughput of about 1 l/h and a phase ratio of 1:160. Compared to example 2, the n-pentanal throughput was halved under otherwise identical reaction conditions.

Table 3 reports the experimental results of the aldolization at three reaction temperatures of 110° C., 120° C. and 130° C., and a pressure of 5 bar. In continuous operation after a time of 3 hours in the steady state, the following results were obtained:

TABLE 3

Aldolization of n-pentanal in a reaction mixing pump

| Reaction conditions | | | |
|---|---|---|---|
| n-Pentanal (l/h) | 1 | 1 | 1 |
| Temperature (° C.) | 110 | 120 | 130 |
| PR (l of starting material/l of cat. phase) | 1:160 | 1:160 | 1:160 |
| Product composition | | | |
| n-Pentanal (% by mass) | 4.05 | 3.03 | 2.77 |
| n-Pentanol (% by mass) | 0.10 | 0.10 | 0.11 |
| 2-Propylheptenal (% by mass) | 89.98 | 91.69 | 95.37 |
| $C_{10}$-aldols (% by mass) | 1.37 | 0.57 | 0.35 |
| High boilers/miscellaneous (% by mass) | 1.22 | 1.36 | 1.40 |
| n-Pentanal conversion (%) | 95.9 | 96.9 | 97.2 |
| Selectivity (%) | 97.8 | 98.6 | 98.7 |

As can be seen from the table, the n-pentanal conversions could be improved compared to example 2 by reducing the n-pentanal throughout. In this way, high n-pentanal conversions of about 97% at selectivities of >98% were achieved at reaction temperatures of 120° C. and 130° C.

Example 4

According to the Invention

Preparation of 2-Propylheptenal from N-Pentanal in a Reaction Mixing Pump

In the following example, the influence of increasing the NaOH circulation at a constant pentanal throughput on the conversion and selectivity of the aldolization is described. For this purpose the catalyst circulation was varied in the range from 80 to 240 l/h at 120° C. and 5 bar and a pentanal throughput of 2 l/h.

Table 4 shows the experimental results of the aldolization at a constant aldehyde throughput for three of the circulation settings 80, 160 and 240 l/h. In continuous operation after a time of three hours in the steady state, the following results were obtained:

TABLE 4

Aldolization of n-pentanal in a reaction mixing pump

| Reaction conditions | | | |
|---|---|---|---|
| n-Pentanal (l/h) | 2 | 2 | 2 |
| Temperature (° C.) | 120 | 120 | 120 |
| NaOH circulation (l/h) | 80 | 160 | 240 |
| PR (l of starting material/l of cat. phase) | 1:40 | 1:80 | 1:120 |
| Product composition | | | |
| n-Pentanal (% by mass) | 6.56 | 5.24 | 5.22 |
| n-Pentanol (% by mass) | 0.11 | 0.10 | 0.11 |
| 2-Propylheptenal (% by mass) | 89.39 | 91.69 | 91.94 |
| $C_{10}$-aldols (% by mass) | 2.65 | 1.88 | 1.61 |
| High boilers/miscellaneous (% by mass) | 1.10 | 1.09 | 1.13 |
| n-Pentanal conversion (%) | 93.4 | 94.7 | 94.7 |
| Selectivity (%) | 96.3 | 97.4 | 97.7 |

As can be seen from the table, increasing the circulation from 80 to 160 and 240 l/h, corresponding to an increase in the phase ratio from 1:40 to 1:80 and 1:120, led to a significant increase in the n-pentanal conversion from 93.4% to 97.7%.

The invention claimed is:

1. A process for preparing an α,β-unsaturated aldehyde, comprising:
    reacting, in a catalytic aldol condensation in a reactor, a starting aldehyde, in presence of an aqueous base, and maintaining continuous flow through the reactor during reacting,
    wherein the reactor is a reaction mixing pump.
2. The process of claim 1, wherein the reaction mixing pump comprises:
    a) a fixed pump housing,
    b) an impeller configured to rotate in the pump housing and comprising a plurality of radially extending mixing chambers which are open in a direction of a circumference of the impeller,
    c) a mixing channel which encloses the mixing chambers and extends within the pump housing along the circumference of the impeller,
    d) an inlet for a reaction starting material,
    e) an outlet for a reaction product, the outlet connected to the inlet, thereby allowing fluid flow by the mixing channel, and
    f) a motor configured to rotate the impeller.
3. The process of claim 2, further comprising:
    adding the starting aldehyde and the aqueous base through a joint inlet or separate inlets into the mixing channel while the impeller is rotating, wherein catalytic aldol condensation occurs within the mixing channel and the α,β-unsaturated aldehyde leaves the mixing channel through the outlet.

4. The process of claim 3, wherein the catalytic aldol condensation is exclusively within the mixing channel.

5. The process of claim 3, wherein the impeller rotates at a circumferential velocity greater than an average flow velocity of a reaction mixture along the mixing channel.

6. The process of claim 3, wherein the catalytic aldol condensation comprises maintaining a temperature in the mixing channel of from 50 to 180° C.

7. The process of claim 3, wherein a mass ratio of the aqueous base to the starting aldehyde in the inlet is from 20 to 400.

8. The process of claim 3, wherein a residence time in the reaction mixing pump is from 0.1 to 2 seconds.

9. The process of claim 3, wherein the starting aldehyde comprises a pentenal and the α,β-unsaturated aldehyde comprises a decenal.

10. The process of claim 9, wherein the starting aldehyde is a $C_5$-aldehyde mixture having an n-pentanal content of at least 90% by mass.

11. The process of claim 10, wherein the starting aldehyde is a $C_5$-aldehyde mixture having an n-pentanal content of at least 95% by mass.

12. The process of claim 9, wherein a temperature in the mixing channel is from 110° C. to 140° C.

13. The process of claim 9, wherein a mass ratio of the aqueous base to the starting aldehyde in the inlet is from 40 to 240.

14. The process of claim 9, wherein a residence time in the reaction mixing pump is from 0.1 to 1.5 seconds.

15. The process of claim 9, further comprising:

phase separating the reaction product at a temperature of from 70 to 120° C.

16. The process of claim 3, wherein the aqueous base is an alkali metal hydroxide.

17. The process of claim 16, wherein the aqueous base comprises sodium hydroxide.

18. The process of claim 17, further comprising:

discharging a portion of the sodium hydroxide of the catalytic aldol condensation to obtain a recycled sodium hydroxide mixture, and introducing fresh sodium hydroxide and the recycled sodium hydroxide mixture into the reaction mixing pump, wherein the recycled sodium hydroxide mixture comprises a sodium salt of a carboxylic acid, the starting aldehyde comprises a pentenal, and the α,β-unsaturated aldehyde comprises a decenal.

19. The process of claim 9, wherein a pressure of the catalytic aldol condensation is from 0.1 to 2 MPa.

* * * * *